United States Patent [19]
Fritsch et al.

[11] Patent Number: 6,069,285
[45] Date of Patent: May 30, 2000

[54] ALKYLAROMATIC PROCESS USING A SOLID ALKYLATION CATALYST AND A BENZENE RECTIFIER

[75] Inventors: Thomas R. Fritsch, Villa Park; Steven F. Eshelman, Elmhurst; Dennis E. O'Brien, Arlington Heights, all of Ill.

[73] Assignee: UOP LLC, Des Plaines, Ill.

[21] Appl. No.: 09/329,087

[22] Filed: Jun. 9, 1999

Related U.S. Application Data

[60] Provisional application No. 60/088,675, Jun. 9, 1998.

[51] Int. Cl.$^7$ .......................... C07C 2/64; C07C 15/067; C07C 15/107; C07C 1/00
[52] U.S. Cl. ..................... 585/449; 585/450; 585/455; 585/323; 585/446
[58] Field of Search ..................... 585/449, 450, 585/455, 323, 446

[56] References Cited

U.S. PATENT DOCUMENTS

| | | | |
|---|---|---|---|
| 5,276,231 | 1/1994 | Kocal et al. | 585/323 |
| 5,648,579 | 7/1997 | Kulprathipanja et al. | 585/447 |
| 5,998,687 | 12/1999 | Woodle et al. | 585/449 |

OTHER PUBLICATIONS

*Handbook of Petroleum Refining Processes* edited by Robert A. Meyers, (McGraw–Hill, New York, 2$^{nd}$ Ed., 1997) pp. 1.53–1.66 and pp. 5.11–5.19.

Primary Examiner—Marian C. Knode
Assistant Examiner—Thuan D. Dang
Attorney, Agent, or Firm—John G. Tolomei; Michael A. Moore

[57] ABSTRACT

An integrated alkylaromatic process using a solid alkylation catalyst and an aromatic rectifier is disclosed for alkylating aromatics with olefins and for regenerating the solid alkylation catalyst. The aromatic rectifier produces a relatively low-purity aromatic-containing overhead stream that is used in producing alkylaromatics, and an aromatic column produces a relatively high-purity aromatic-containing overhead stream that is used in regenerating the solid alkylation catalyst. In another embodiment, this process is further integrated with a paraffin dehydrogenation zone and an aromatic by-products removal zone. This invention produces the benzene-containing streams that are necessary for alkylating and for regenerating in a more economical manner than prior art processes.

20 Claims, 1 Drawing Sheet

ALKYLAROMATIC PROCESS USING A SOLID ALKYLATION CATALYST AND A BENZENE RECTIFIER

CROSS-REFERENCE TO RELATED APPLICATION

This application claims the benefit of U.S. Provisional Application No. 60/088,675, filed Jun. 9, 1998.

FIELD OF THE INVENTION

The invention relates to the alkylation of aromatic compounds with olefins using solid catalyst.

BACKGROUND OF THE INVENTION

About thirty years ago it became apparent that household laundry detergents made of branched alkylbenzene sulfonates were gradually polluting rivers and lakes. Solution of the problem led to the manufacture of detergents made of linear alkylbenzene sulfonates (LABS), which were found to biodegrade more rapidly than the branched variety. Today, detergents made of LABS are manufactured worldwide.

LABS are manufactured from linear alkylbenzenes (LAB). The petrochemical industry produces LAB by dehydrogenating linear paraffins to linear olefins and then alkylating benzene with the linear olefins in the presence of HF. This is the industry's standard process. Over the last decade, environmental concerns over HF have increased, leading to a search for substitute processes employing catalysts other than HF that are equivalent or superior to the standard process. Solid alkylation catalysts, for example, are the subject of vigorous, ongoing research.

To date, alkylation processes that use catalysts other than HF, that is, commercially available solid alkylation catalysts, tend to operate at a higher molar ratio of benzene per olefin than processes that employ HF. As an illustration, while detergent alkylation processes that use HF tend to operate at a benzene/olefin molar ratio of 12:1 to 6:1, alkylation processes that use commercially available solid alkylation catalysts tend to run at higher benzene/olefin ratios, typically 30:1 to 20:1. One reason for this is that solid alkylation catalysts tend to be less selective toward producing monoalkylbenzene, and therefore the benzene/olefin molar ratio must be increased to meet increasingly stringent selectivity requirements. Selectivity, which is often defined as the weight ratio of monoalkylbenzene product to all products, is expected in some areas to be 85–90% near term, increasing to 90–95% by about the year 2000. Incidentally, a higher benzene/olefin ratio not only tends to increase selectivity but also often produces other benefits for solid alkylation catalysts, including improving olefin conversion, monoalkylbenzene linearity, and catalyst life.

As desirable as solid catalyst may be as an alternative to liquid HF, it is commonly the case that these catalysts deactivate with use. Alkylation processes, with either HF or substitute catalysts for HF, are subject to catalyst deactivation. Whereas an alkylation process employing HF typically employs an HF regenerator, an alkylation process employing a substitute catalyst such as a solid alkylation catalyst typically includes means for periodically taking the catalyst out of service and regenerating it by removing the gum-type polymers that accumulate on the surface of the catalyst and block reaction sites. For a solid alkylation catalyst, therefore, the catalyst life is measured in terms of time in service at constant conversion between regenerations. The longer the time between regenerations, the more desirable the catalyst and the process.

Although all catalysts lose some portion of their activity with continued use, the solid catalysts used to date in aromatic alkylation tend to deactivate rather quickly. Although the deactivation can be retarded by increasing alkylation reaction temperature, raising the reaction temperature tends to decrease product linearity, which is an undesirable outcome. Conversely, lowering the reaction temperature increases product linearity, a desirable result, but exacerbates catalyst deactivation leading to short useful catalyst lifetimes. As has already been suggested, catalyst life can be increased by operating at higher benzene/olefin ratio, but raising the benzene/olefin ratio increases the cost of building and operating an alkylation process, in terms of both investment capital and utilities costs. Thus, it is clear that solid catalyst can be best used in the continuous alkylation of aromatics only where effective and inexpensive means of catalyst regeneration are available.

Solid catalysts used for alkylation of aromatic compounds by olefins, especially those in the 6 to 20 carbon atom range, usually are deactivated by by-products which are preferentially adsorbed by the catalysts. Such by-products include, for example, polynuclear hydrocarbons in the 10 to 20 carbon atom range formed in the dehydrogenation of $C_6$ to $C_{20}$ linear paraffins and also include products of higher molecular weight than the desired monoalkyl benzenes, e.g., di- and tri-alkyl benzenes, as well as olefin oligomers. Although it can be readily appreciated that such catalyst deactivating agents or "poisons" are an adjunct of aromatic alkylation, fortunately it has been observed that deactivating agents can be readily desorbed from the catalyst by washing the catalyst with the aromatic reactant. Thus, catalyst reactivation, or catalyst regeneration as the term is more commonly employed, is conveniently effected by flushing the catalyst with aromatic reactants to remove accumulated poisons from the catalyst surface, generally with restoration of 100% of catalyst activity.

Therefore, it is imperative to have means of repeatedly regenerating these catalysts, i.e., to restore their activity, in order to utilize their catalytic effectiveness over long periods of time. It is further desirable to minimize the additional equipment required for regeneration and that is not used for normal operation, that is for the production of alkylaromatics. That is, one desires that any equipment that is used for alkylaromatic production be capable of a dual use for alkylation catalyst regeneration.

It is still further desirable, when converting a process unit from HF catalyst to solid alkylation catalyst, to maximize the use of equipment that exists and is in use in the HF alkylation process. Therefore, it is useful to briefly review one configuration of an HF detergent alkylation unit that gained wide acceptance during the 1970's and 1980's. That configuration uses an HF alkylation reaction section, an HF regeneration section, and an HF sludge treatment section. It is not necessary here to describe these three sections in detail, but one of the compelling reasons for switching from HF to a solid catalyst is that building and operating these three HF-containing sections have often proven to be troublesome, complex, and expensive. In addition to these three sections, this HF detergent alkylation unit also uses a series of five product recovery columns to produce a monoalkylbenzene product stream from the alkylation reaction effluent, which contains not only monoalkylbenzene but generally also benzene, paraffins, by-products, and HF. The first of the five product recovery columns is usually called an HF stripper, which strips HF from the alkylation reaction effluent for recycle to the HF alkylation reactor. The second column is generally called a benzene column, which is a distillation column that removes benzene from the HF stripper bottom stream as an overhead stream which is recycled to the HF alkylation reactor. Then, the remaining hydrocarbons flow to a series of three distillation columns: a paraffin column which removes the paraffins as a sidecut for recycle to a paraffin dehydrogenation unit if present, an LAB rerun column which removes LAB from the paraffin column bottom stream and produces an overhead stream containing the LAB product, and a heavy alkylate rerun column that removes heavy alkylate by-products including polyalkylbenzenes.

Changing from HF to a solid catalyst has greatly diminished the utility of this five-column product recovery train in existing HF detergent alkylation units, particularly in two aspects. First, the change to a solid catalyst eliminates the need for HF stripping, thereby rendering the existing HF stripper redundant. Second, the higher benzene/olefin molar ratio (e.g., 20:1 as opposed to 8:1) in the alkylation reactor more than doubles the flow of benzene to the existing benzene column, thereby flooding the existing benzene column. Too small for the higher recycle benzene flow, the existing benzene column must be replaced or supplemented with an entirely new benzene column, which greatly increases the capital cost of converting from HF to solid catalyst. But, even if a new benzene column was not needed, the operating costs of the now-converted solid catalyst unit would be much higher, because of the additional cost of the energy required to distill and condense the larger quantity of excess benzene from the alkylation reaction effluent.

Accordingly, an integrated continuous alkylation process with a method of removing catalyst deactivation agents or minimizing catalyst deactivation is sought. Such a process can increase the usefulness of commercially available solid alkylation catalyst and will help avoid the need for using HF in detergent alkylation processes.

SUMMARY OF THE INVENTION

In a broad embodiment, this invention is an integrated process for producing alkyl aromatics by alkylating aromatics with olefins using a solid alkylation catalyst and for regenerating deactivated solid alkylation catalyst. In another embodiment, this invention is an integrated process for producing alkyl aromatics from paraffins and aromatics, for regenerating deactivated solid alkylation catalyst, and in addition for preventing catalyst-deactivating by-products from contacting the solid alkylation catalyst. In this invention, the effluent of a solid catalyst alkylation reactor producing alkyl aromatics (e.g., detergent-grade alkyl aromatics) passes to a rectifier, which produces a relatively low-purity aromatic-containing (e.g. benzene-containing) overhead stream which is suitable for recycling to an on-stream solid catalyst reactor. The rectifier provides an economical way of maintaining a relatively high molar ratio of aromatic (e.g., benzene) per olefin in an on-stream solid catalyst, thereby helping to retard deactivation and extend the life of the solid alkylation catalyst. The bottom stream of the rectifier passes to an aromatic fractionation column, which produces a relatively high-purity aromatic-containing (e.g., benzene-containing) overhead stream which is suitable for passing to an off-stream alkylation reactor containing deactivated catalyst which is undergoing regeneration. Although some capital and operating costs are incurred in producing this relatively high-purity stream, the aromatic column does not needlessly recycle only the relatively high-purity stream to the on-stream alkylation reactor. Thus, savings accrue to the extent that the relatively low-purity rectifier overhead stream, instead of the relatively high-purity fractionation column overhead stream, is recycled to the on-stream alkylation reactor. In another aspect, this invention can be further integrated with a sorptive removal unit for removing aromatic by-products formed during paraffin dehydrogenation, because the overhead stream of the benzene fractionation column is also suitable for regenerating an off-stream sorptive bed in the sorptive removal unit.

When applied to a detergent alkylation process, the present invention uses the rectifier to decrease the cost of recycling benzene to alkylation reactors that are producing detergent alkylate. The higher the benzene/olefin molar ratio in the on-stream detergent alkylation reactor, the greater is the benefit of this invention. This benefit arises not only because rectification is a more economical method of separating the alkylation reactor effluent than the fractionation columns employed in the prior art processes, but also because rectification produces a recycle stream that is sufficiently, but not overly, pure benzene-containing stream for recycling to the on-stream detergent alkylation reactor. All other factors being the same, the energy consumed in distillation tends to increase as the desired purity of the distillate stream increases. Thus, by using less of the relatively high-purity overhead stream from the benzene column when the relatively low-purity overhead stream from the benzene rectifier suffices, this invention decreases the costs of recycling benzene to the alkylation reactor. Accordingly, the benzene rectifier zone bottom stream passes to a fractionation column, commonly known as the benzene column, which removes most of the remaining benzene that was in the alkylation reactor effluent and produces a benzene column overhead stream having a higher purity than that of the overhead stream produced by the benzene rectifier. Of course, it is within the scope of this invention that some of the benzene column overhead stream may be recycled to the on-stream detergent alkylation reactor, but the benefit of this invention is greatest when the flow of relatively high-purity benzene from the benzene column overhead to the on-stream alkylation reactor is minimized.

One of the significant ways in which this invention can reduce the costs associated with recycling benzene to an on-stream alkylation reactor is by significantly decreasing the size of the benzene column. By removing some of the benzene from the on-stream alkylation reactor effluent prior to passing the remainder of the reactor effluent to the benzene column, the diameter, height, and reboiler duty of the benzene column are reduced, because the benzene throughput through the benzene column has been decreased. Although new solid catalyst alkylation units can benefit from this advantage, this advantage has far-reaching implications for solid catalyst alkylation processes that are built by converting existing HF detergent alkylation processes to solid alkylation catalysts. This is because enough benzene can be removed from the alkylation reactor effluent using the benzene rectifier that the remaining benzene in the benzene rectifier bottom stream is not greater than the benzene content of in the HF stripper bottom stream in an HF alkylation process. Therefore, with the use of a benzene rectifier between the alkylation reactor effluent and the benzene column, the entire existing fractionation train of an existing HF alkylation process can be re-used when the catalyst is switched from HF to a solid alkylation catalyst, resulting in large savings in investment capital for converting to a solid catalyst alkylation unit. Additional savings are possible because the existing HF stripper of the HF alkylation process can be readily modified and then used as the benzene rectifier in the solid alkylation process and therefore much of the cost of a new benzene rectifier is avoided.

Accordingly, in one embodiment, this invention is a process for producing alkylaromatics. Olefins and feed aromatics are reacted to form alkylaromatics in an on-stream alkylation zone in the presence of solid alkylation catalyst at alkylation conditions. The alkylation conditions are sufficient to at least partially deactivate at least a portion of the solid alkylation catalyst in the on-stream alkylation zone. An on-stream effluent stream comprising alkylaromatics and feed aromatics is withdrawn from the on-stream alkylation zone. At least a portion of the on-stream effluent stream passes to a rectifier. In the rectifier, the at least a portion of the on-stream effluent stream is separated into a rectifier overhead stream comprising feed aromatics and depleted in alkylaromatics and a rectifier bottom stream comprising feed aromatics and enriched in alkylaromatics. At least a portion of the rectifier overhead stream is recycled to the on-stream alkylation zone. At least a portion of the rectifier bottom stream passes to a fractionation zone. In the fractionation zone, the at least a portion of the rectifier bottom stream is separated into a fractionation overhead stream comprising feed aromatics and depleted in alkylaromatics and a fractionation bottom stream comprising feed aromatics and enriched in alkylaromatics. Alkylaromatics are recovered from the fractionation bottom stream. At least a portion of the fractionation overhead stream comprising feed aromatics passes to an off-stream alkylation zone containing at least partially deactivated solid alkylation catalyst. The at least a portion of the fractionation overhead stream contacts partially deactivated solid alkylation catalyst in the off-stream alkylation zone to partially regenerate the solid alkylation catalyst and to produce at least partially regenerated solid alkylation catalyst in the off-stream alkylation zone. An off-stream effluent stream comprising feed aromatics is withdrawn from the off-stream alkylation zone. At least a portion of the off-stream effluent stream passes to the rectifier or the fractionation zone. Periodically the functions of the on-stream and off-stream alkylation zones are shifted by operating the off-stream alkylation zone to function as the on-stream alkylation zone and operating the on-stream alkylation zone to function as the off-stream alkylation zone.

Additional embodiments are described in the following description of this invention.

INFORMATION DISCLOSURE

LAB processes are described in the book edited by Robert A. Meyers entitled *Handbook of Petroleum Refining Processes*, (McGraw-Hill, New York, Second Edition, 1997) at pages 1.53 to 1.66, the teachings of which are incorporated herein by reference. Paraffin dehydrogenation processes are described in the Meyers book at pages 5.11 to 5.19, the teachings of which are incorporated herein by reference.

U.S. Pat. No. 5,648,579 (Kulprathinpanja et al.) teaches that solid catalyst used for the alkylation of aromatic compounds by olefins usually are deactivated by by-products which are preferentially adsorbed by the solid catalysts, and that the deactivating agents can be readily desorbed from the solid alkylation catalyst by washing the catalyst with the aromatic reactant.

U.S. Pat. No. 5,276,231 (Kocal et al.) teaches an alkylaromatic process with removal of aromatic by-products which are normally formed in paraffin dehydrogenation. In particular, U.S. Pat. No. 5,276,231 teaches sorbing the aromatic by-products on a sorbent such as a molecular sieve, and contacting the sorbent with liquid benzene to regenerate the sorbent. The teachings of U.S. Pat. No. 5,276,231 are incorporated herein by reference.

DETAILED DESCRIPTION OF THE INVENTION

In a broad embodiment, this invention is an integrated process for producing alkyl aromatics by alkylating aromatics with olefins using a solid alkylation catalyst and for regenerating deactivated solid alkylation catalyst. The feedstocks which are used in the practice of this embodiment of the invention normally result from the dehydrogenation of paraffins. The entire dehydrogenation reaction mixture often is used with the dehydrogenation reaction not being run to completion to minimize cracking, isomerization, and other undesirable and deleterious by-products. The polyolefins formed during dehydrogenation are minimized in the feedstocks used in the practice of this invention. Consequently the feedstocks are a mixture largely of unreacted paraffins, branched monoolefins, and unbranched or linear monoolefins. These paraffins and monoolefins typically are in the $C_6$–$C_{22}$ range, although those in the $C_8$–$C_{16}$ range are preferred in the practice of this invention, and those in the $C_{10}$–$C_{14}$ range are even more preferred. The monoolefins in the feedstock are reacted with benzene or alkylated derivatives of benzene that are charged to the subject process. Suitable alkylated derivatives of benzene (alkylaromatics) include, but are not limited to, toluene, xylenes, and higher methylated benzenes; ethylbenzene, diethylbenzene, and triethylbenzenes; isopropylbenzene (cumene), n-propylbenzene, and higher propylbenzenes; butylbenzenes; and pentylbenzenes. Thus, the alkylated derivative of benzene may have one or more alkyl groups, and each alkyl group may have from 1 to 5 or even more carbon atoms.

The most widely practiced alkylaromatic process to which the present invention is applicable is the production of linear alkylbenzenes (LAB). Therefore, the discussion herein of the present invention will be in reference to its application to an LAB process. It is not intended that this discussion limit the scope of the present invention as set forth in the claims.

The LAB process is a well-established hydrocarbon conversion process described in the book by Robert A. Meyers entitled *Handbook of Petroleum Refining Processes*, (McGraw-Hill, New York, Second Edition, 1997) at pages 1.53 to 1.66 and 5.11 to 5.19. Thus the art of LAB processes is well known and does not require detailed description herein.

In an LAB process, normal paraffins are usually charge to the dehydrogenation reactor. Any branched olefins which are formed in dehydrogenation usually are not removed, yet the total amount of nonlinear alkylbenzene formed still must be sufficiently small that the monoalkylate meets the requirements of, say, 90% linearity. Branched monoolefins in the feedstock are usually present in small (about 2 mol-%) concentrations. As for the linear or unbranched monoolefins in the feedstock, unsaturation may appear anywhere on the linear monoolefin chain, since there is no requirement as to the position of the double bond, but only a requirement as to the linearity of the olefin. The linear monoolefins in the feedstock are reacted with benzene, since the product of alkylating a linear monoolefin with an alkylated derivative of benzene may not be as suitable a detergent precursor as alkylated benzene. Although the stoichiometry of the alkylation reaction requires only 1 molar proportion of benzene per mole of total linear monoolefins, the use of a 1:1 mole proportion results in excessive olefin polymerization and polyalkylation. That is, the reaction product under such conditions would consist not only of the desired monoalkylbenzenes, but also large amounts of the dialkylbenzenes, trialkylbenzenes, possibly higher polyalkylated benzenes, olefin dimers, trimers, etc., and unreacted benzene. On the other hand, it is desired to have the benzene:olefin molar ratio as close to 1:1 as possible to maximize benzene utilization and to minimize the recycle of unreacted benzene. The actual molar proportion of benzene to total monoolefins will therefore have an important effect both on conversion and, perhaps more importantly, on selectivity of the alkylation reaction. In order to carry out alkylation with the conversion, selectivity, and linearity required using the catalysts of our process, a total benzene-:linear monoolefin molar ratio of from 5:1 up to as high as 30:1 is recommended, although the process normally operates satisfactorily at a total benzene:linear monoolefins molar ratio between about 8:1 and about 20:1.

The benzene and linear monoolefins are reacted in the presence of a solid alkylation catalyst under alkylation conditions. These alkylation conditions include a temperature in the range between about 176° F. (80° C.) and about 284° F. (140° C.), most usually at a temperature not exceeding 275° F. (135° C.). Since the alkylation is conducted as a liquid phase process, pressures must be sufficient to maintain the reactants in the liquid state. The requisite pressure necessarily depends upon the feedstock and temperature, but normally is in the range of 200–1000 psi(g) (1379–6895 kPa(g)), and most usually 300–500 psi(g) (2069–3448 kPa(g)).

Solid alkylation catalysts typically are characterized as having an acid function and are, therefore, better known as solid acid catalysts. Such solid acid catalysts include, but are not limited to, materials such as amorphous silica-alumina, crystalline aluminosilicate materials such as zeolites and molecular sieves, naturally occurring and man-made clays including pillared clays, sulfated oxides such as sulfonated zirconia, traditional Friedel-Crafts catalyst such as aluminum chloride and zinc chloride, and solid Lewis acids generally. The nature of the solid alkylation catalyst is not critical to the success of this invention and is largely a matter of choice to be made by the practitioner. Solid alkylation catalysts are illustrated in U.S. Pat. No. 3,201,487 issued to S. Kovach et al.; U.S. Pat. No. 4,358,628 issued to L. Slaugh; U.S. Pat. No. 4,489,213 issued to S. Kovach; U.S. Pat. No. 4,673,679 issued to D. Farcasiu; U.S. Pat. No. 5,003,121 issued to Imai et al. which discloses an extruded catalyst comprising clay and at least one multi-valent metal; U.S. Pat. No. 5,034,564 issued to J. A. Kocal which discloses a catalyst comprising a pillared clay and a binder; U.S. Pat. Nos. 5,196,574 and 5,344,997, both issued to J. A. Kocal, which disclose a fluorided silica-alumina catalyst; U.S. Pat. No. 5,302,732 issued to K. Z. Steigleder et al which describes an ultra-low sodium silica-alumina catalyst; and U.S. Pat. No. 5,491,271 issued to Marinangeli et al. which discloses the use of either delaminated or pillared tetrahedrally charged clays. Zeolitic solid alkylation catalysts are disclosed in U.S. Pat. Nos. 3,751,506; 4,387,259; and 4,409,412; and in addition in U.S. Pat. No. 5,019,670 and U.S. Pat. No. 5,132,477, which disclose using MCM-22 to alkylate aromatics with olefin oligomers; and also in U.S. Pat. Nos. 4,301,317 and 4,301,316, which describe catalyzing detergent alkylation with crystalline aluminosilicates. Silica-aluminas used as a support for various metals in the alkylation of aromatics with olefins include U.S. Pat. Nos. 3,169,999; 3,201,487; 4,358,628; and 4,870,222; European Patent Application No. 0160145; Japanese Patent Application J02237641-A; and articles by Kurosaki and Okazaki in *Bull Chem. Soc. Japan*, 63, 2363 (1990) and *Chemistry Letters*, 589 (1991).

The effluent of the alkylation reaction zone, which has a molar ratio of benzene per alkylaromatic of from about 5:1 to about 30:1, passes to a rectifier. It is well known that a rectifier differs distinctly from a stripper both in appearance and function. The differences between a rectifier and a stripper are readily apparent by considering distillation processes in general. Distillation processes rely on the well-known tendency that when liquid and vapor phases contact, the more volatile components tend to concentrate more in the vapor phase than in the liquid phase. In single-stage operation, this concentration of the more volatile component in the vapor phase is achieved by partially vaporizing a liquid mixture and then separating the liquid and vapor phases. In multi-stage operation, a liquid descends a vertical distillation column and passes through a number of stages in which it is contacted countercurrently by ascending vapor. The point at which feed is introduced to the distillation column divides the column into two sections. The stripping section is below the feed point, and the rectifying section is above the feed point. In the stripping section, the more volatile component is stripped from the descending liquid. In the rectifying section, the concentration of the less volatile component in the vapor is reduced. In practice, the stages in which the streams of liquid and vapor contact each other may be trays or packing material. Therefore, in a rectifier the feed is at the bottom of a number of stages, in comparison to a stripper where the feed to a stripper is at the top of a number of stages. Furthermore, a rectifier reduces the concentration of the less volatile component in the vapor, whereas a stripper strips the more volatile component from the descending liquid. Thus, a rectifier functions differently from a stripper. Accordingly, a person of ordinary skill in the art views a rectifier as distinct method of separation and therefore would not replace a rectifier with a stripper.

The rectifier has generally from about 10 to about 20 separation stages and usually uses sieve trays with a tray efficiency of about 60%. Thus, the rectifier generally has from about 15 to about 25 trays, and typically 20 trays. Fewer than 15 trays could be used, and some or all of the trays could be replaced with a vapor-liquid contacting media, such as regular-shaped Berl saddles or Raschig rings in a random arrangement or such as structured elements in an ordered arrangement. The benzene rectifier usually employs a reboiler, either external or internal to the benzene rectifier, a feed preheater, or both. When used, a reboiler for the benzene rectifier is normally located below the lowermost separation stage or tray. The reboiler normally comprises bayonet-style heat exchanger tubes inserted into the benzene rectifier, but the reboiler may also be external to the benzene rectifier, with conduits carrying fluids back and forth between the reboiler and the benzene rectifier. A heating fluid, typically hot oil or steam, circulates through the bayonet tubes and is collected from the tubes. Contact of the hydrocarbons with the tubes may be either in flow-through mode or in backmix mode. The benzene rectifier typically also employs a total condenser. As used herein, the term "total condenser" means a heat exchanger which condenses a vapor or mixture of vapors, condensing generally more than 95 wt-%, and more commonly more than 99.5 wt-% of the vapors. A portion of the condensed overhead stream is typically refluxed to the upper portion of the benzene rectifier, usually to a location above the uppermost tray of the benzene rectifier. The remaining portion of the condensed overhead stream recycles to an on-stream alkylation reactor. As used herein in the context of a portion of a stream, the term "portion" means an aliquot portion or a nonaliquot portion, unless otherwise stated. An aliquot portion of a stream is a portion of the stream that has essentially the same composition as the stream. The vessel shell of the benzene rectifier typically comprises unlined killed carbon steel. Internal equipment within the benzene rectifier, such as trays, baffles, and the reboiler, have a similar metallurgy.

The operating conditions of the benzene rectifier include a pressure of from about 50 to about 70 psi(g) (345 to 483 kPa(g)), although higher pressures up to the design limit of the vessel may be employed. The overhead temperature of the benzene rectifier is normally about 300° F. (149° C.) and the bottom temperature is generally also about 300° F. (149° C.). Thus, the benzene rectifier operates with a relatively small difference between the overhead and bottom temperatures, which is a consequence of the abundance of benzene in the benzene rectifier. Despite driving a substantial amount of benzene from the alkylation reactor effluent into the benzene rectifier overhead stream, the benzene rectifier generally produces a bottom stream that nevertheless contains a sufficient amount of benzene such that the boiling point of the bottom stream is relatively close to that of the overhead stream. Of the total amount of benzene entering the benzene rectifier with the alkylation reactor effluent, generally about 50 percent to about 70 percent exits with the net overhead stream and the remainder exits with the net bottoms stream.

The purity of the benzene-containing stream which is recovered from the net overhead of the benzene rectifier is relatively low in comparison with the hereinafter described purity of the benzene-containing stream which is recovered from the net overhead of the benzene column. The benzene-containing net stream recovered from the overhead of the benzene rectifier generally has a benzene concentration of from about 80 to about 98 mol-%. For the benzene rectifier overhead stream, the concentration of paraffins is generally from 2 to 20 mol-% and preferably from 2 to 5 mol-%, and the concentration of alkylated benzenes (alkylaromatics) is generally less than 100 wppm. The presence of paraffins in contact with the catalyst at normal alkylation temperatures is believed to not have a significant detrimental effect on the solid alkylation catalysts, although the paraffins are substantially unreactive in the alkylation reactor and their presence occupies volume in the reactor that could otherwise be used for producing alkylated benzenes. Thus, although the presence of the paraffins in the alkylation reactor may necessitate the use of a slightly larger reactor volume in order to accommodate the hydraulic requirements that arise as a result of recycling the paraffins, it is believed that the recycling of the paraffins does not have a deleterious effect on the catalytic activity of the solid alkylation catalyst. Accordingly, despite its paraffin content, the net overhead liquid stream of the benzene rectifier is a suitable source of benzene for recycling a portion or an aliquot portion thereof to the alkylation reactor. However, as will be explained hereinafter, this net overhead stream of benzene is believed to be unsuitable for use in regenerating deactivated solid alkylation catalyst.

The paraffins present in the net overhead stream of the benzene rectifier generally have from 5 to 22 carbon atoms. The particular paraffins present depend primarily on the compositions of two streams that are introduced to the subject process and of one stream that may be used in an embodiment of the subject process. The first source of paraffins present in the benzene rectifier net overhead stream is the paraffins that are introduced into the alkylation reaction zone with the monoolefin-containing feedstock. Such paraffins typically have the same number of carbon atoms as that of the monoolefins in the feedstock, that is typically in the broad $C_6$–$C_{22}$ range, but also possibly in the narrower ranges of $C_8$–$C_{16}$ or $C_{10}$–$C_{14}$. A second origin of paraffins in the benzene rectifier net overhead stream is the benzene-containing charge stream that is charged to the alkylation zone. The paraffins in this benzene charge stream have boiling points that are generally close to that of benzene, and thus have generally between 6 and 9 carbon atoms. If, as described hereinafter, the benzene charge stream is introduced to the benzene column, and if any entering $C_8$–$C_9$ paraffins are rejected from the benzene column bottom and only the $C_6$–$C_7$ paraffins are withdrawn from the benzene column overhead, then only $C_6$–$C_7$ paraffins will be charged to the alkylation reaction zone and will ultimately appear in the benzene rectifier net overhead stream. Finally, as also described hereinafter, if an aromatic by-products removal zone using a $C_5$–$C_8$ paraffinic purge stream is employed in an integrated process that employs the subject invention, $C_5$–$C_8$ paraffins of the purge stream may pass to the alkylation reaction zone and may also be present in the benzene rectifier overhead stream. Thus, $C_5$–$C_{22}$ paraffins may be present in the net overhead stream of the benzene rectifier.

The net bottom stream of the benzene rectifier, which has a molar ratio of benzene per alkylaromatic of about 7:1, passes to the benzene column. The benzene column, which removes the remainder of the benzene using typically from 45 to 55 sieve trays, usually about 50 sieve trays. The benzene rectifier bottoms stream enters at or around sieve tray 30, as numbered from the top of the benzene column. Makeup benzene, which need not be previously dried, is also fed to the benzene column, typically at a location in the upper portion of the benzene column, within 5 or 10 trays from the top of the benzene column. Both the makeup benzene and the benzene rectifier bottoms streams are generally in the liquid phase. The benzene column usually employs a reboiler as well as a total condenser for the overhead stream, which refluxes liquid to the top of the benzene column. The operating conditions of the benzene column include a pressure of about 10 psi(g) (69 kPa(g)), an overhead temperature of about 200° F. (93° C.), and a bottom temperature of about 450° F. (232° C.). The benzene column produces a net overhead stream which has a benzene concentration of usually more than 95 mol-%, preferably more than 99.9 mol-%, and more preferably more than 99.99 mol-%. The benzene column net overhead stream may also contain a small concentration of paraffins of generally less than 5 mol-%, preferably less than 0.1 mol-%, more preferably less than 100 wppm, and even more preferably less than 10 wppm. In the benzene column net overhead stream, alkylated benzenes (alkylaromatics), if any, are generally present at lower concentrations than that of paraffins. Thus, as has already been stated, the purity of the benzene stream recovered from the overhead of the benzene column is generally greater than that of the benzene stream recovered from the overhead of the benzene rectifier.

Like the net overhead stream of the benzene rectifier, the net overhead stream of the benzene column may contain paraffins having from 5 to 22 carbon atoms. Also, as in the case of the benzene rectifier, the particular paraffins present in the benzene column net overhead stream depend primarily on the paraffins in the monoolefinic feedstock, the benzene-containing charge, and the purge stream, if any, of an aromatic by-products removal zone, if used.

In accord with this invention, a portion such as an aliquot portion of the net overhead liquid stream of the benzene column is passed to an off-stream alkylation reactor containing solid alkylation catalyst that is undergoing reactivation or regeneration. It is believed that the purity of the benzene that is used for regeneration of the solid alkylation catalyst is an important variable, in combination with the regeneration temperature, for insuring that the regenerated catalyst is returned to an acceptable level of activity for alkylating reactions. Without being bound to any particular theory, it is believed that the presence of paraffins in contact with the alkylation catalyst at the relatively high temperatures employed during regeneration has a detrimental effect on the catalyst. Therefore, it is believed that the net overhead liquid stream of the benzene column, with its lower paraffin concentration relative to the net overhead liquid stream of the benzene rectifier, is a suitable stream for regenerating deactivated solid alkylation catalyst.

Thus in a preferred embodiment, the net overhead liquid stream of the benzene column is passed to a bed of solid alkylation catalyst which is undergoing regeneration. The effluent of the reactor that is undergoing regeneration contains benzene, paraffins, alkylated benzenes, and heavy components desorbed from the catalyst. Although this effluent stream from the off-stream alkylation reactor could be passed to the benzene rectifier in the same manner as the alkylation reactor effluent during normal operation, it is preferred that this regeneration effluent stream passes to the benzene column. Thus, the benzene column may be fed not only with benzene from the bottom of the benzene rectifier, and makeup benzene, but also benzene from the alkylation reactor that is undergoing regeneration.

In another embodiment, this invention is an integrated process for producing alkyl aromatics by dehydrogenating linear paraffins to linear olefins and then alkylating benzene with the linear olefins in the presence of a solid alkylation catalyst, for regenerating deactivated solid alkylation catalyst, and in addition for preventing catalyst-deactivating by-products from contacting the solid alkylation catalyst.

The dehydrogenation section will preferably be configured substantially in the manner shown in the drawing of U.S. Pat. No. 5,276,231. A feed stream containing paraffins combines with recycled hydrogen and recycled unreacted paraffins from the alkylation section. This forms a reactant stream which is heated and passed through a bed of a suitable catalyst maintained at the proper dehydrogenation conditions of temperature, pressure, etc. Dehydrogenation catalysts are well known in the dehydrogenation art, as exemplified by U.S. Pat. Nos. 3,274,287; 3,315,007; 3,315,008; 3,745,112; and 4,430,517, and need not be described here in great detail. The nature of the dehydrogenation catalyst is not critical to the success of our invention and is largely a matter of choice to be made by the practitioner. The effluent of this catalyst bed or reactor effluent stream is usually cooled, partially condensed, and passed to a vapor-liquid or product separator. The condensed material, referred to herein as the dehydrogenated product stream, passes to a stripping separation zone which usually includes a stripping column that removes all compounds which are more volatile than the lightest normal hydrocarbon which it is desired to charge to the alkylation section of the process. The stripping column produces a net bottoms stream referred to herein as the stripping effluent stream.

The stripping effluent stream is passed to the alkylation section, which comprises a selective alkylation zone and a fractionation or alkylate recovery zone, such as described previously. In the selective alkylation zone, the linear olefins in the stripping effluent stream react with an aromatic, which is generally benzene, to produce a selective alkylation zone effluent stream containing linear alkylbenzene. In the manner already described and in accord with the broad embodiment of this invention, the selective alkylation zone effluent passes to the benzene rectifier, and the rectifier bottom stream passes to the fractionation column called the benzene column. The bottom stream of the benzene column enters additional separation facilities for the recovery of products and recyclable feed compounds. In one commonly employed arrangement, the bottom stream of the benzene column passes to a paraffin column which produces an overhead liquid stream containing unreacted paraffins, which normally is recycled as a recycle stream to the dehydrogenation zone, and a bottoms stream containing the product alkylate and any higher molecular weight side product hydrocarbons formed in the selective alkylation zone. This bottoms stream is passed into a rerun column which produces an overhead alkylate product stream containing the detergent alkylate and a bottoms stream containing polymerized olefins and polyalkylated benzenes (heavy alkylate).

A common variant of this embodiment includes the selective hydrogenation of diolefins that are normally present in the dehydrogenated product stream or the stripping effluent stream. It is well known that diolefins are formed during the catalytic dehydrogenation of paraffins. Selective diolefin hydrogenation converts diolefins to monoolefins, which are the desired product of the dehydrogenation section, and produces a selective diolefin hydrogenation product stream. Selective diolefin hydrogenation is taught in U.S. Pat. Nos. 4,520,214 and 5,012,021, the teachings of both of which are incorporated herein by reference.

Another common variant of this embodiment includes the selective hydrogenation of monoolefins that are normally present in the overhead liquid stream of the paraffin column. It is well known that unreacted monoolefins from the selective alkylation zone are present in the overhead liquid stream, and that these monoolefins shorten the life of currently available dehydrogenation catalysts where the overhead liquid stream is recycled to the dehydrogenation zone. Selective monoolefin hydrogenation converts the monoolefins to paraffins, which are the desired feed compound of the dehydrogenation section, and produces a selective monoolefin hydrogenation product stream.

An aromatics removal zone eliminates or significantly reduces the aromatic by-products in the feedstock to the selective alkylation zone in the present embodiment for the production of alkylated aromatic compounds. Removal of the aromatic by-products reduces the deactivation rate of solid alkylation catalyst and, thereby, produces a significantly higher yield of linear alkylated aromatic compounds.

It is well known that aromatic by-products are formed during the catalytic dehydrogenation of paraffins. For instance, the article starting at page 86 of the Jan. 26, 1970, issue of "Chemical Engineering" states that the product of the dehydrogenation of linear paraffins includes aromatic compounds. The nature of the particular aromatic by-products that are formed in dehydrogenation is not essential to this invention. These aromatic by-products are believed to include, for example, alkylated benzenes, naphthalenes, other polynuclear aromatics, alkylated polynuclear hydrocarbons in the $C_{10}$–$C_{15}$ range, indanes, and tetralins, that is, they are aromatics of the same carbon number as the paraffin being dehydrogenated and may be viewed as aromatized normal paraffins. The particular side reactions that lead to the formation of the aromatic by-products are also not essential to this invention. An illustration of some of the parallel thermal cracking reactions that can lead to the formation of aromatic by-products is found in the diagram at the bottom of page 5.12 of the previously mentioned book by Robert A. Meyers entitled *Handbook of Petroleum Refining Processes*. Typically, from about 0.2 to about 0.7 weight percent, and generally to the extent of no more than 1 weight percent, of the feed paraffinic compounds to a dehydrogenation zone form aromatic by-products. Although some commercially available dehydrogenation catalysts are more selective than others at minimizing the formation of aromatic by-products, it is believed that these by-products are formed at least to a small extent at suitable dehydrogenation conditions in the presence of most, if not all, commercially available dehydrogenation catalysts. Since it is an economic advantage to operate the dehydrogenation zone at conditions that produce a high conversion of the feed paraffinic compounds and a high yield of the desired olefins, these aromatic by-products are produced at least to a small extent in most if not all commercial dehydrogenation zones. In processes without removal of aromatic by-products, the concentration of aromatic by-products in the stripping effluent stream can typically accumulate to 4–10 weight percent, which leads to rapid deactivation of solid alkylation catalyst.

This embodiment of the invention selectively removes at least a portion of the aromatic by-products in the dehydrogenated product stream using at least one aromatics removal zone. An aromatics removal zone may be placed in one or more locations in the prior art processes. First, the aromatic by-products may be selectively removed from the dehydrogenated product stream and the stripping effluent stream. Second, where the overhead liquid stream of the paraffin column is recycled to the dehydrogenation zone, which is normally the case in commercial applications, the aromatic by-products may be selectively removed from the recycle stream. Third, where the subject process includes a selective monoolefin hydrogenation zone, the aromatic by-products may be selectively removed from the selective monoolefin hydrogenation product stream. Fourth, where the subject process includes a selective diolefin hydrogenation zone, the aromatic by-products may be selectively removed from the selective diolefin hydrogenation product stream. The aromatics removal zone is preferably located between the dehydrogenation zone and the selective alkylation zone because the aromatic by-products are preferably selectively removed prior to entering the selective alkylation zone. These locations set forth above are not necessarily equivalent in terms of the required equipment, such as heaters, heat exchangers, vessels, coolers, and etc. to practice our invention. Those skilled in the art of hydrocarbon processing are able to design and provide the required equipment.

Suitable aromatics removal zones for this embodiment of the invention include sorptive separation zones. Where the aromatics removal zone is a sorptive separation zone, our invention can be practiced in fixed bed or moving sorbent bed systems, but the fixed bed system is preferred. The sorbent may be installed in one or more vessels and in either series or parallel flow. The flow of the stream containing the aromatic by-products through the sorptive separation zones is preferably performed in a parallel manner so that when one of the sorbent beds or chambers is spent by the accumulation of the aromatic by-products thereon, the spent zone may be by-passed while continuing uninterrupted operation through the parallel zone. Although the spent sorbent may be replaced, in this embodiment of the invention the spent zone of sorbent is regenerated using the benzene column overhead stream.

Suitable sorbents may be selected from materials which exhibit the primary requirement of selectivity for the aromatic by-products and which are otherwise convenient to use. Suitable sorbents include, for example, molecular sieves, silica, activated carbon activated charcoal, activated alumina, silica-alumina, clay, cellulose acetate, synthetic magnesium silicate, macroporous magnesium silicate, and/or macroporous polystyrene gel. It should be understood that the above-mentioned sorbents are not necessarily equivalent in their effectiveness. The choice of sorbent will depend on several considerations including the capacity of the sorbent to retain aromatic by-products, the selectivity of the sorbent to retain the aromatic by-products which are more detrimental to solid alkylation catalysts, and the cost of the sorbent. The preferred sorbent is a molecular sieve, and the preferred molecular sieve is 13 X zeolite (sodium zeolite X). Detailed descriptions of zeolites may be found in the book authored by D. W. Breck entitled "Zeolite Molecular Sieves" published by John Wiley, and Sons, New York, in 1974.

Those skilled in the art are able to select the appropriate conditions for operation of the sorbent without undue experimentation. For example, a fixed bed sorptive separation zone containing 13 X zeolite may be maintained at a temperature generally from about 68° F. to about 572° F. (20° C. to 300° C.) and preferably from about 212° F. to about 392° F. (100° C. to 200° C.), a pressure effective to maintain the stream containing the aromatic by-products in a liquid phase at the chosen temperature. and a liquid hourly space velocity from about 1 $hr^{-1}$ to about 10 $hr^{-1}$ and preferably from about 1 $hr^{-1}$ to about 3 $hr^{-1}$. The flow of the stream containing the aromatic by-products through the sorptive separation zone may be conducted in an upflow, downflow or radial-flow manner.

Although both liquid and vapor phase operations can be used in many sorptive separation processes, liquid phase operation is preferred for the sorptive separation zone because of the lower temperature requirements and because of the higher sorption yields of the aromatic by-products that can be obtained with liquid phase operation over those obtained with vapor phase operation. Therefore, the temperature and pressure of the sorptive separation zone during sorption of the aromatic by-products are preferably selected to maintain in a liquid phase the stream from which the aromatic by-products are selectively removed. Alternatively, the temperature and pressure of the sorptive separation zone during sorption of the aromatic by-products can be selected to maintain in a liquid phase the aromatic by-products in the stream from which the aromatic by-products are selectively removed. Mixed phases (i.e., a combination of a liquid phase and a vapor phase) for the stream from which the aromatic by-products are separated are generally not preferred because of the well-known difficulties involved in maintaining uniform flow distribution of both a liquid phase and a vapor phase through a sorptive separation zone. The resulting unsorbed stream having a reduced concentration of aromatic by-products is then passed on in the process. However, the operating conditions of a sorptive separation zone can be optimized by those skilled in the art to operate over wide ranges which are expected to include the conditions in the reaction zones of our invention and its variants. Therefore, this embodiment of our invention includes a sorptive separation zone contained in a common reaction vessel with the dehydrogenation zone, the selective diolefin hydrogenation zone, the selective alkylation zone or the selective monoolefin hydrogenation zone.

Following an appropriate processing period which will depend on the composition of the stream containing the aromatic by-products and the particular aromatic by-products themselves, it is usually necessary to regenerate the sorbent, that is to remove the sorbed aromatic by-products from the sorbent so that the sorbent may be reused. There are numerous methods of regenerating the sorbent using the benzene column overhead stream, and it is not intended to limit this invention to any particular method of regenerating the sorbent. Any suitable regeneration method may be used, including altering the temperature and pressure of the sorbent and treating with the benzene column overhead stream as a gas or a vapor, as a liquid, or as both a vapor or gas and a liquid to displace or desorb the sorbed aromatic by-products.

Those skilled in the art are able to select the appropriate conditions for regeneration of the sorbent without undue experimentation. The flow direction of the benzene column overhead stream through the sorptive separation zone may be upflow or radial flow, but the preferred direction is downflow. The phase of the benzene column overhead stream mixture through the sorptive separation zone may be liquid phase, vapor phase, or a mixture of liquid and vapor phases.

An effluent stream is withdrawn from the aromatics removal zone which contains benzene, a purge hydrocarbon such as pentanes where the zone was purged with a purge hydrocarbon prior to being contacted with the benzene column overhead stream, and aromatic by-products produced during dehydrogenation that became sorbed on the sorbent in the aromatics removal zone. This effluent stream is typically passed to a desorbent fractionation column, which produces a heavy bottom stream comprising the aromatic by-products. If the benzene column overhead stream contains any feed paraffins, these feed paraffins would be present in the effluent stream, and would ultimately appear in the heavy bottom stream of the desorbent column. This is because the aromatics by-products and the paraffins generally have the same carbon number, and hence both the aromatic by-products and the paraffins co-boil at approximately the same temperature, and are, therefore, recovered in the same bottom stream of the desorbent column. Because the paraffins, which can potentially be converted into desirable alkylated aromatics, and the aromatic by-products, which cannot be readily converted into the desired alkylaromatics, are recovered in the same stream, because both groups of compounds co-boil, therefore, the rejection of the aromatic by-products from the desorbent column results also in the rejection of the paraffins. The higher the concentration of paraffins in the benzene column overhead stream to the aromatics removal zone, the greater is the loss of these paraffins from the desorbent column with the aromatic by-products. It is for this reason that it is preferred that the regeneration stream for the aromatics removal zone come from the net overhead liquid of the benzene column rather than the net overhead liquid of the benzene rectifier because of its higher purity.

The desorbent column also produces a net overhead stream which contains the lighter components, namely benzene and a purge compound such as pentane. This net overhead stream passes to a fractionation column which separates the purge compound from the benzene. In the case where the purge compound is pentane, this separation zone is a depentanizing fractionation column, which produces a net overhead stream comprising pentanes and a net bottom stream comprising benzene. The net overhead stream is recovered for use in purging the aromatics removal zone, and the net bottom stream is recycled to the solid catalyst alkylation zone. In this manner, some of the benzene requirements for the solid catalyst alkylation zone is supplied by the fractionation column downstream of the desorbent column associated with the aromatics removal zone, which in the aforementioned case is a depentanizer.

Accordingly, in an integrated process for the production of alkyl aromatics that uses dehydrogenation and an aromatics removal zone, and an alkylation section which employs a benzene rectifier and a benzene column for recovering the alkyl aromatics, a preferred embodiment of this invention is one in which the regeneration method for the sorbent in the aromatics removal zone comprises altering the temperature and pressure of the sorbent and treating the sorbent with a liquid to displace or desorb the sorbed aromatic by-products. The liquid for desorbing the aromatic by-products is the net overhead liquid stream of the benzene column. The net overhead liquid stream of the benzene rectifier, with its lower purity and higher concentration of paraffins, is not employed for regenerating the sorbent in the aromatics removal zone. This is because the paraffins contained in the benzene rectifier net overhead liquid stream are ultimately lost from the process and represent an economic loss because they are not employed in making valuable detergent alkylation product. Accordingly, in this integrated process embodiment of this invention, the benzene column overhead stream contains preferably less than 0.1 mol-% paraffins, more preferably less than 100 wppm paraffins, and even more preferably less than 10 wppm paraffins.

Figure 1:
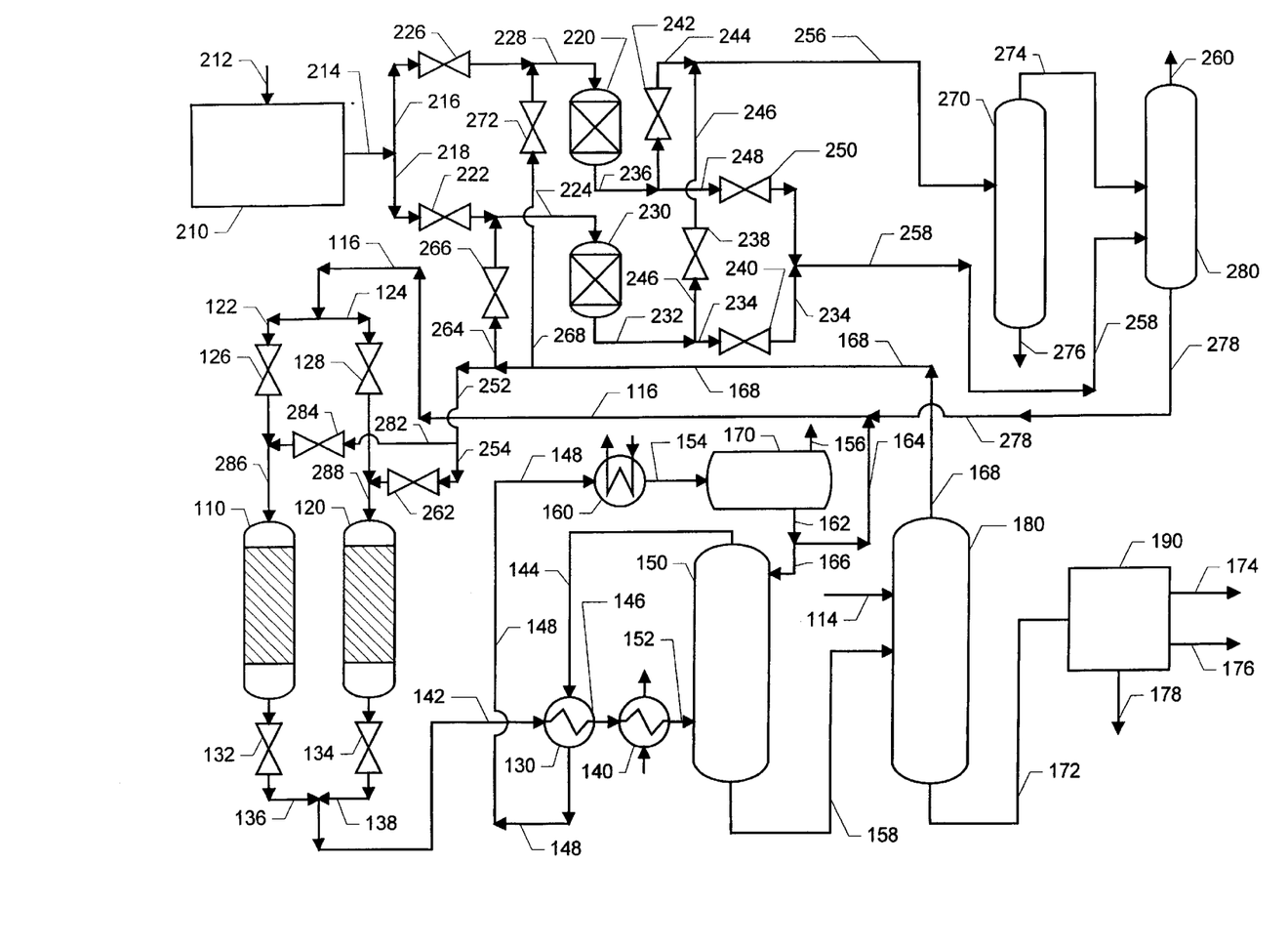
The drawing is a process flow diagram of an embodiment of this invention.

A complete operation of the process can be more fully understood from a process flow for a preferred embodiment. The drawing depicts only the equipment that is necessary for an understanding of this invention, and accordingly conventional equipment that is within the skill of a person of ordinary skill in the art of hydrocarbon processing, such as pumps, instrumentation, some heat exchangers, and some valves. The description of this invention in the context of this specific embodiment is not meant to limit the scope of this invention to the embodiment shown herein.

Referring now to the drawing, a paraffin feed stream comprising an admixture of $C_{10}$–$C_{15}$ normal paraffins is charged to line 212. Although the paraffin feed stream may contain paraffins having 7 or fewer carbon atoms, the concentration of such paraffins is preferably minimized. The normal paraffins are usually combined with a hereinafter described stream of recycle paraffins from line 174, although the combination of these two streams is not shown in the drawing. The paraffins enter a dehydrogenation section 210, where the paraffins are contacted with a dehydrogenation catalyst in the presence of hydrogen at conditions which effect the conversion of a significant amount of the paraffins to the corresponding olefins. The product of the dehydrogenation section comprises monoolefins, unreacted paraffins, and aromatic by-products and passes through line 214. A zone for aromatic by-product removal is depicted schematically in the drawing as consisting of two sorptive beds, with bed 230 on-stream for removing aromatic by-products and bed 220 off-stream for regeneration of the sorbent. In practice, however, commercial processes may at any given time use two or more beds on-stream arranged in parallel or in series with two or more beds off-stream in various stages of regeneration. Valve 222 is open and valve 226 is closed. The dehydrogenation section product passes through lines 218 and 224 and enters on-stream bed 230, which removes aromatic by-products. The effluent of bed 230 flows through lines 232, 234, and 258 to depentanizer column 280, valve 240 being open and valve 250 being closed. Most of the olefinic and paraffinic hydrocarbons entering depentanizer 280 through line 258 are heavier than pentane, and therefore exit via the bottom of depentanizer 280 through line 278. Preferably, the concentration of C$_7$-minus paraffins in the bottom stream in line 278 is small. The hydrocarbons in line 278 combine with the benzene-containing net overhead liquid stream from benzene rectifier 150, which flows through line 164.

The combined stream of olefins, paraffins, and benzene flows through lines 116, 122, and 286 to alkylation reactor 110. Two alkylation reactors 110 and 120 are depicted in the drawing, with reactor 110 on-stream for alkylating benzene with olefins and reactor 120 off-stream for regeneration of the solid alkylation catalyst. At any given time, commercial processes may use two or more series-flow or parallel-flow on-stream reactors with two or more off-stream reactors undergoing regeneration. Valve 126 is open and valve 128 is closed. Valve 132 is open, and so the on-stream reactor effluent passes through lines 136. Valve 134 is also open, and so the on-stream reactor effluent in line 136 combines with the hereinafter described off-stream reactor effluent flowing through line 138. The combined stream flows through line 142, is heated in heat exchanger 130, flows through line 146, is further heated in heat exchanger 140, flows through line 152, and enters benzene rectifier 150. In heat exchanger 130 heat is supplied from the benzene rectifier overhead vapor stream in line 144, and an external heated stream, such as hot oil or steam, supplies heat in heat exchanger 140. After passing through heat exchanger 130, the benzene-containing overhead vapor stream in line 148 of the benzene rectifier 150 is further condensed in condenser 160, flows through line 154, and enters overhead receiver 170. A small net stream of light, uncondensed hydrocarbons is withdrawn from receiver 170 via line 156. The liquid from receiver 170 flows through line 162, and splits into two portions. One portion returns to the benzene rectifier 150 as reflux, and the other portion combines with the olefins and paraffins in line 278 and recycles to the on-stream alkylation reactor 110 as described previously.

The benzene rectifier bottom stream flows through line 158 to benzene fractionation column 180. The benzene fractionation column 180 is a separate vessel from the benzene rectifier 150. A benzene-containing makeup stream enters benzene column 180 through line 114. Although the benzene-containing makeup stream in line 114 may contain C$_6$–C$_7$ paraffins including cycloparaffins, the concentration of such paraffins in the make-up stream is preferably minimized. The bottom stream of the benzene column 180 flows through line 172 to conventional product recovery facilities 190. The streams withdrawn from recovery facilities 180 include a paraffin recycle stream 174, a heavy alkylate stream 178, and an alkylaromatic product stream 176. The net overhead stream of the benzene column 180 is condensed by a condenser which is not shown in the drawing, and the net condensed liquid flows in line 168. The net liquid, which preferably contains a minimum of C$_6$ and C$_7$ paraffins, splits into two portions. One portion regenerates the sorbent in off-stream bed 220 and the other portion regenerates the solid alkylation catalyst in off-stream reactor 120. Accordingly, one portion of the stream in line 168 flows through lines 268 and 228 to bed 220, valve 272 being open and valve 266 being closed. Thus, with bed 220 being off-stream there is no flow through line 216, and with bed 230 being on-stream there is no flow through line 264.

The effluent of bed 220 is not only enriched in aromatic by-products desorbed from bed 220 but also typically contains a C$_5$–C$_8$ paraffin, such as pentane. Such a paraffin is typically used to purge olefins from an aromatic by-products removal bed after the bed has been taken off-stream and before the bed has been regenerated with benzene. The effluent flows through lines 236, 244, and 256 to desorbent column 270, valve 242 being open and valve 250 being closed. Because bed 220 is off-stream with valve 250 closed, there is no flow through line 248, and because bed 230 is on-stream with valve 238 closed there is no flow through line 246. Desorbent column 270 produces a bottom stream 276 comprising aromatic by-products which is withdrawn from the process and can be used for fuel. The desorbent column also produces an overhead stream 274 comprising benzene and pentanes which flows to depentanizer 280. Depentanizer column 280 produces an overhead stream 260 comprising pentane, which is routed to storage facilities (not shown) for maintaining a pentane inventory available for purging sorptive bed 246 when that bed is taken off-stream.

Pentane, as previously suggested, is a common purge compound for the aromatic by-products removal beds, and therefore this description of the drawing refers to the use of pentane. For example, column 280 in the drawing is referred to herein as the depentanizer column. However, it is not intended that this description limit the scope of the invention as set forth in the claims. Accordingly, one or more other purge compounds in addition to or instead of pentane could also have been used, in which case column 280 would have been referred to in this description by another name, such as a deoctanizer if octane is the purge compound or as a dehexanizer/deheptanizer if a mixture of hexanes and heptanes is used for purging. Regardless of the particular purge compound(s) used, the column 280 produces an overhead stream 260 containing the purge compound(s), which is routed to a purge compound inventory storage facilities (not shown). Although the bottom stream 278 may contain purge compound(s) because the separation in the column 280 may not be perfect, the concentration of purge compound(s) in the bottom stream 278 is preferably minimized.

The other portion of the benzene-containing stream in line 168 flows through lines 252, 254, and 288, and into off-stream reactor 120. Valve 262 is open and valve 284 is closed. With reactor 120 being off-stream and reactor 110 being on-stream, there is no flow through line 282 nor is there flow through line 124. The benzene entering reactor 120 washes heavy by-products from the alkylation catalyst that cause the catalyst to deactivate. Thus, the effluent from off-stream reactor 120 contains benzene as well as these by-products, which can include polynuclear hydrocarbons, polyalkylated aromatics, and olefin oligomers. In the embodiment shown in the drawing, valve 134 is open when reactor 120 is off-stream, so that the effluent in line 138 combines with the effluent from on-stream reactor 110 and flows to the benzene rectifier 150 and benzene column 180. The benzene in the effluent of off-stream reactor 120 is recovered in either the overhead stream of benzene rectifier 150, the overhead stream of benzene column 180, or both. The by-products in effluent of off-stream reactor 120 tend to concentrate in the bottom streams of benzene rectifier 150 and benzene column 180, and are ultimately recovered by product recovery facilities 190 in the heavy alkylate stream 178. As an alternative to flowing to benzene rectifier 150, the effluent of off-stream reactor 120 could instead bypass the benzene rectifier 150 and flow directly to benzene column 180.

The arrangement of the lines and valves upstream and downstream of the reactors 110 and 120 permit the functions of the on-stream reactor 110 and the off-stream reactor 120 to be periodically shifted, so that the on-stream reactor 110 functions as the off-stream reactor 120 and the off-stream reactor 120 functions as the on-stream reactor 110. This shifting of functions is performed when the catalyst in the on-stream reactor 110 becomes sufficiently deactivated as to render continued on-stream operation impractical or uneconomical, or when the catalyst in the off-stream reactor 120 becomes sufficiently reactivated as to render it to be practicably or economically operated on-stream, or both. This shifting of functions can be accomplished by opening the valves 128 and 284 which are closed and closing the valves 126 and 262 which are open. In an analogous manner, the arrangement of the lines and valves upstream and downstream of the beds 220 and 230 also permit the functions of the on-stream bed 230 and the off-stream bed 220 to be periodically shifted, so that the on-stream bed 230 functions as the off-stream bed 220 and the off-stream bed 220 functions as the on-stream bed 230.

A variation of the process flow shown in the drawing can be used when the benzene-containing net overhead liquid stream in line 164 from the benzene rectifier 150 contains light paraffins. "Light paraffins" as used in this context means paraffins having up to one carbon atom more than the number of carbon atoms of the aromatic substrate that reacts with the monoolefins in the alkylation reactor 110 or 120. Thus, for example, in the case of LAB production where monoolefins react with benzene, "light paraffins" means paraffins having 7 or fewer carbon atoms. If the monoolefins react with toluene "light paraffins" means paraffins having 8 or fewer carbon atoms, and "light paraffins" means paraffins having 9 or fewer carbon atoms where the monoolefins react with xylenes. Light paraffins that are passed to the alkylation reactor 110 or 120 tend to be present in the effluent 142 of the alkylation reactor 110 or 120, and in turn tend to concentrate in the overhead of the benzene rectifier 150. Of course, some light paraffins, such as methane and ethane, are uncondensed at the typical operating conditions of the benzene rectifier's overhead condenser 160 and receiver 170, and these light paraffins are withdrawn from the receiver 170 via the line 158, as described previously. But, light paraffins having one fewer carbon atom, one more carbon atom, or the same number of carbon atoms as the aromatic substrate (e.g., benzene) are generally difficult to separate from the aromatic substrate by rectification. So, for example, in an LAB process light paraffins including $C_5$–$C_7$ paraffins are condensed in condenser 160, collect in the liquid phase in receiver 170, and thus are recycled with benzene to the alkylation reactor 110 or 120 via lines 164 and 116. Without some method for removing them, these light paraffins might accumulate to unacceptable concentrations in the recycle circuit that includes the alkylation reactor 110 or 120, the benzene rectifier 150, the benzene rectifier overhead receiver 170, and the interconnecting equipment and lines.

Accordingly, a variation of the process flow shown in the drawing provides a method for rejecting light paraffins from the recycle circuit comprising the alkylation reactor 110 or 120, the benzene rectifier 150, and the overhead receiver 170. In this variation, a slip stream or a portion such as an aliquot portion of the net overhead liquid stream in line 164 passes to a light paraffin distillation column (not shown in the drawing). The light paraffin distillation column separates the entering stream into an overhead stream comprising light paraffins (e.g., $C_5$–$C_7$ paraffins) and a bottom stream comprising the aromatic substrate (e.g., benzene). The bottom stream may also comprise paraffins that are heavier than the light paraffins. At least a portion of the overhead stream may be passed through a line (not shown) and introduced into the dehydrogenation section 210, for example via line 212 by combining with the paraffin feed stream. Alternatively, at least a portion of the overhead stream may be rejected from the process. At least a portion of the bottom stream may be passed through a line (not shown) and recycled to the alkylation reactor 110 or 120, by, for example, combining with the depentanizer bottom stream flowing in the line 278. Alternatively, at least a portion of the bottom stream may be recycled to benzene column 180 by, for example, combining with the benzene rectifier net bottom stream flowing in line 158.

What is claimed is:

1. A process for producing alkylaromatics comprising:

a) reacting olefins and feed aromatics to form alkylaromatics in an on-stream alkylation zone in the presence of solid alkylation catalyst at alkylation conditions, the alkylation conditions being sufficient to at least partially deactivate at least a portion of the solid alkylation catalyst in the on-stream alkylation zone, and withdrawing from the on-stream alkylation zone an on-stream effluent stream comprising alkylaromatics and feed aromatics;

b) passing at least a portion of the on-stream effluent stream to a rectifier, and separating the at least a portion of the on-stream effluent stream in the rectifier into a rectifier overhead stream comprising feed aromatics and depleted in alkylaromatics and a rectifier bottom stream comprising feed aromatics and enriched in alkylaromatics;

c) recycling at least a portion of the rectifier overhead stream to the on-stream alkylation zone;

d) passing at least a portion of the rectifier bottom stream to a fractionation zone, separating the at least a portion of the rectifier bottom stream into a fractionation overhead stream comprising feed aromatics and depleted in alkylaromatics and a fractionation bottom stream comprising feed aromatics and enriched in alkylaromatics;

e) recovering alkylaromatics from the fractionation bottom stream;

f) passing at least a portion of the fractionation overhead stream comprising feed aromatics to an off-stream alkylation zone containing at least partially deactivated solid alkylation catalyst, contacting the at least partially deactivated solid alkylation catalyst in the off-stream alkylation zone with the at least a portion of the fractionation overhead stream to at least partially regenerate the solid alkylation catalyst and to produce at least partially regenerated solid alkylation catalyst in the off-stream alkylation zone, and withdrawing an off-stream effluent stream comprising feed aromatics from the off-stream alkylation zone;

g) passing at least a portion of the off-stream effluent stream to the rectifier or the fractionation zone; and h) periodically shifting the functions of the on-stream and off-stream alkylation zones by operating the off-stream alkylation zone to function as the on-stream alkylation zone in Steps (a) and (c) and operating the on-stream alkylation zone to function as the off-stream alkylation zone in Step (f).

2. The process of claim 1 further characterized in that the at least a portion of the rectifier overhead stream comprises an aliquot portion of the rectifier overhead stream.

3. The process of claim 1 further characterized in that the at least a portion of the fractionation overhead stream comprises an aliquot portion of the fractionation overhead stream.

4. The process of claim 1 further characterized in that the at least a portion of the rectifier overhead stream has a concentration of feed aromatics of from about 80 to about 98 mol-%.

5. The process of claim 1 further characterized in that the at least a portion of the fractionation overhead stream has a concentration of feed aromatics of greater than about 95 mol-%.

6. The process of claim 1 further characterized in that the olefins comprise olefinic hydrocarbons having from 6 to 22 carbon atoms.

7. The process of claim 1 further characterized in that the feed aromatics comprise benzene and alkylated derivatives of benzene.

8. The process of claim 1 further characterized in that the alkylation conditions comprise a molar ratio of olefins per feed aromatic of from about 5:1 to about 30:1.

9. The process of claim 1 further characterized in that the rectifier and the fractionation zone are contained in separate vessels.

10. The process of claim 1 further characterized in that the rectifier overhead stream has a concentration of alkylaromatics of less than 100 wppm.

11. The process of claim 1 further characterized in that the rectifier overhead stream has a concentration of paraffins of from 2 to 20 mol-%.

12. The process of claim 1 further characterized in that the fractionation overhead stream has a concentration of paraffins of less than 5 mol-%.

13. The process of claim 1 wherein the rectifier overhead stream comprises light paraffins and wherein the recycling of at least a portion of the rectifier overhead stream to the on-stream alkylation zone comprises recycling a first aliquot portion of the rectifier overhead stream to the on-stream alkylation zone, further characterized in that a second aliquot portion of the rectifier overhead stream passes to a light paraffin distillation zone, the light paraffin distillation zone separates the entering hydrocarbons into a distillation overhead stream comprising light paraffins and a distillation bottom stream comprising feed aromatics, at least a portion of the distillation bottom stream is recycled to the on-stream alkylation zone or the fractionation zone, and at least a portion of the distillation overhead stream is rejected from the process.

14. A process for producing alkylaromatics comprising:
a) dehydrogenating a paraffinic feed stream containing $C_6$–$C_{22}$ paraffins in a dehydrogenation zone and recovering therefrom a dehydrogenated product stream containing paraffins, monoolefins, $C_9$-minus hydrocarbons, diolefins, and aromatic by-products;
b) optionally selectively hydrogenating to monoolefins at least a portion of the diolefins in the dehydrogenated product stream in a selective diolefin hydrogenation zone and recovering therefrom a selective diolefin hydrogenation product stream containing paraffins, monoolefins, $C_9$-minus hydrocarbons, and aromatic by-products;
c) passing at least one of (i) the selective diolefin hydrogenation product stream where present and (ii) the dehydrogenated product stream through a stripping separation zone to remove $C_6$-minus hydrocarbons and recovering therefrom a stripping effluent stream containing paraffins, monoolefins, and aromatic by-products;
d) selectively alkylating an aromatic compound by reacting the aromatic compound and monoolefins of the stripping effluent stream at alkylation conditions in an on-stream selective alkylation zone containing a solid alkylation catalyst to form principally alkylated aromatic compounds, the alkylation conditions being sufficient to at least partially deactivate at least a portion of the solid alkylation catalyst in the on-stream selective alkylation zone, and producing an on-stream selective alkylation effluent stream containing alkylated aromatic compounds, aromatic compound, paraffins, monoolefins and aromatic by-products;
e) separating hydrocarbons in the on-stream selective alkylation effluent stream in a rectification zone and recovering a rectification overhead stream containing aromatic compound, paraffins, and aromatic by-products, and a rectification bottom stream containing alkylated aromatic compounds, aromatic compound, paraffins, monoolefins, and aromatic by-products;
f) recycling aromatic compound and paraffins in the rectification overhead stream to the on-stream selective alkylation zone;
g) separating hydrocarbons in the rectification bottom stream in a fractionation zone and recovering a fractionation overhead stream containing aromatic compound and a fractionation bottom stream containing alkylated aromatic compounds, paraffins, monoolefins, and aromatic by-products;
h) recovering from the fractionation bottom stream an alkylate product stream containing alkylated aromatic compounds and a recycle stream containing paraffins, monoolefins, and aromatic by-products;
i) optionally selectively hydrogenating to paraffins the monoolefins in the recycle stream in a selective monoolefin hydrogenation zone and recovering therefrom a selective monoolefin hydrogenation product stream containing paraffins and aromatic by-products;
j) optionally recycling at least a portion of at least one of (i) the selective monoolefin hydrogenation product stream where present and (ii) the recycle stream to the dehydrogenation zone;
k) selectively removing at least a portion of the aromatic by-products from at least one of the dehydrogenated product stream, the selective diolefin hydrogenation product stream, the stripping effluent stream, the recycle stream, and the selective monoolefin hydrogenation product stream in at least one on-stream aromatic by-products removal zone containing a sorbent at sorptive conditions effective to selectively sorb aromatic by-products and reduce the concentration of aromatic by-products in the stripping effluent stream to a level no more than about 2 weight percent;
l) passing a first portion of aromatic compound in the fractionation overhead stream to an off-stream selective alkylation zone containing solid alkylation catalyst, the solid alkylation catalyst in the off-stream selective alkylation zone being at least partially deactivated, to at least partially regenerate the solid alkylation catalyst in the off-stream selective alkylation zone;
m) recovering from the off-stream selective alkylation zone an off-stream selective alkylation effluent stream containing aromatic compound and passing at least a portion of the aromatic compound in the off-stream selective alkylation effluent stream to at least one of (i) the rectification zone and (ii) the fractionation zone;
n) passing a second portion of aromatic compound in the fractionation overhead stream to at least one off-stream aromatic by-products removal zone containing sorbent, the sorbent in the off-stream aromatic by-products removal zone containing sorbed aromatic by-products, to at least partially desorb aromatic by-products from the sorbent in the off-stream aromatic by-products removal zone;

o) recovering from the at least one off-stream aromatic by-products removal zone a reject stream containing aromatic by-products and a desorbent stream containing aromatic compound;

p) periodically shifting the functions of the on-stream selective alkylation zone and the off-stream selective alkylation zone by operating the off-stream selective alkylation zone to function as the on-stream selective alkylation zone and operating the on-stream selective alkylation zone to function as the off-stream selective alkylation zone; and q) periodically shifting the functions of the at least one on-stream aromatic by-products removal zone and the at least one off-stream aromatic by-products removal zone by operating the off-stream aromatic by-products removal zone to function as the on-stream aromatic by-products removal zone and operating the on-stream aromatic by-products removal zone to function as the off-stream aromatic by-products removal zone.

15. The process of claim 14 further characterized in that at least a portion of the aromatic compound in the desorbent stream is passed to the on-stream selective alkylation zone.

16. The process of claim 14 further characterized in that an off-stream aromatic by-products effluent stream containing aromatic compound, aromatic by-products, and a purge compound is recovered from the at least one off-stream aromatic by-products removal zone, the hydrocarbons in the off-stream aromatic by-products effluent stream are separated in a desorbent column, the reject stream is recovered from the desorbent column, a desorbent overhead stream comprising purge compound and aromatic compound is recovered from the desorbent column, the hydrocarbons in the desorbent overhead stream are separated in a depurging column, a depurging overhead stream containing purge compound is recovered from the depurging column, and the desorbent stream is recovered from the depurging column.

17. The process of claim 16 wherein the purge compound comprises pentane.

18. The process of claim 14 further characterized in that a portion of the rectification overhead stream passes to a paraffin distillation zone, the paraffin distillation zone separates the entering hydrocarbons into a distillation overhead stream comprising paraffins and a distillation bottom stream comprising aromatic compound, at least a portion of the distillation bottom stream is recycled to at least one of (i) the on-stream selective alkylation zone and (ii) the fractionation zone.

19. The process of claim 18 further characterized in that at least a portion of the distillation overhead stream passes to the dehydrogenation zone.

20. The process of claim 14 further characterized in that the fractionation overhead stream has a concentration of paraffins of less than 0.1 mol-%.

* * * * *